United States Patent [19]

Meier et al.

[11] Patent Number: 5,292,960
[45] Date of Patent: Mar. 8, 1994

[54] PROCESS FOR PURIFICATION OF CYCLOHEXANONE

[75] Inventors: Heinz-Peter Meier, Kapellen; Jan van Esbroeck, Kalmthout; Eddy Terweduwe, Berchem, all of Belgium

[73] Assignee: Bayer Aktiengesellschaft, Leverkusen, Fed. Rep. of Germany

[21] Appl. No.: 19,502

[22] Filed: Feb. 19, 1993

[30] Foreign Application Priority Data

Feb. 25, 1992 [DE] Fed. Rep. of Germany ........ 4205633

[51] Int. Cl.⁵ .............................................. C07C 45/85
[52] U.S. Cl. ...................................... 568/366; 568/350
[58] Field of Search ........................... 568/350, 361, 366

[56] References Cited

U.S. PATENT DOCUMENTS

| | | | |
|---|---|---|---|
| 3,251,753 | 5/1966 | Mueller et al. | 568/361 |
| 4,417,076 | 11/1983 | Rozovsky et al. | 568/361 |
| 4,484,005 | 11/1984 | Thomisson | 568/350 |
| 4,670,605 | 6/1987 | Chiu et al. | 568/361 |
| 4,918,239 | 4/1990 | Wang et al. | 568/361 |
| 5,041,682 | 8/1991 | Hartig et al. | 568/361 |

FOREIGN PATENT DOCUMENTS

| | | | |
|---|---|---|---|
| 0714128 | 4/1968 | Belgium | 568/361 |
| 0133696 | 3/1985 | European Pat. Off. | 568/361 |
| 1221619 | 7/1966 | Fed. Rep. of Germany | 568/361 |
| 1188584 | 11/1969 | Fed. Rep. of Germany | 568/361 |
| 1618407 | 12/1970 | Fed. Rep. of Germany | 568/361 |
| 1214522 | 12/1970 | United Kingdom | 568/361 |
| 1420511 | 1/1976 | United Kingdom | 568/361 |

*Primary Examiner*—James H. Reamer
*Attorney, Agent, or Firm*—Sprung Horn Kramer & Woods

[57] ABSTRACT

Cyclohexanone which has been obtained by dehydrogenation of a cyclohexanone/cyclohexanol mixture is substantially freed from by-products, in that such a dehydrogenation mixture is treated in the gas or liquid phase with hydrogen on a hydrogenation catalyst at 20° to 180° C. and at a pressure of 0.1 to 15 bar.

11 Claims, No Drawings

PROCESS FOR PURIFICATION OF CYCLOHEXANONE

BACKGROUND OF THE INVENTION

1. Field of the Invention

The invention relates to a process for the purification of cyclohexanone which has been obtained by dehydrogenation of a cyclohexanone/cyclohexanol mixture, using hydrogen at elevated temperature and at reduced to elevated pressure.

Cyclohexanone which can be used in the process according to the invention can be obtained, for example, by first oxidising cyclohexane with oxygen in the presence of catalytically acting metal salts or in the presence of boric acid to obtain a reaction mixture which contains, inter alia, cyclohexanone, cyclohexanol and, possibly, its boric ester and cyclohexyl hydroperoxide. After thermal decomposition or decomposition by catalytic hydrogenation of the peroxides, and after separating off the constituents mentioned from the oxidation mixture, a cyclohexanone/cyclohexanol mixture is obtained. If cyclohexanone is the desired end product, this mixture, with or without preceding separation of cyclohexanone already present, is dehydrogenated, so that the cyclohexanol fraction is likewise converted into cyclohexanone. However, such a cyclohexanone still contains impurities in the range of 0.5 to 5 $^o/_{oo}$, which are in part of unsaturated nature, but are also in part not completely known.

Furthermore, a cyclohexanone/cyclohexanol mixture can be obtained by hydrogenation of phenol, the cyclohexanol fraction of which mixture can likewise be dehydrogenated in the described manner to give cyclohexanone. Such a cyclohexanone also contains undesired accompanying substances, some unsaturated, in the range mentioned.

The impurities contained in such a cyclohexanone can only be partially eliminated, or not at all, even with great effort. However, they interfere with the following further processing of the cyclohexanone, for example in the subsequent preparation of caprolactam.

2. Description of the Related Art

Considerable efforts have already been made to separate off the impurities mentioned, with or without preceding isomerisation. Thus it has been disclosed to treat the cyclohexanone, obtained in the above manner, with alkali metal hydroxides, alkali metal alcoholates, phenolates or their solutions or with basic ion exchangers and then to rectify the mixtures, or to add auxiliary materials of the type mentioned during the rectification (German Auslegeschrift 1 188 584). However, the presence of compounds having alkaline reaction induces uncontrollable condensation reactions which not only lead to further impurities, but also represent considerable yield losses.

Since a portion of the interfering compounds are of unsaturated nature, attempts have already been made to convert these under hydrogenating conditions either into cyclohexanone or into compounds more easily separated off. This relates, for example, to the particularly interfering compounds cyclohexene and the various cyclohexenones. However, in all hitherto known hydrogenation processes, a large fraction of the cyclohexanone has always been further reduced to give cyclohexanol, for example according to BE 714 128, in which a catalytic gas-phase hydrogenation prior to the purification by distillation is disclosed; an examination showed that further by-products result here which must be additionally eliminated. It seemed, therefore, that a hydrogenating purification at various stages of the process for cyclohexanone preparation would remain unsuccessful. According to EP 411 455, therefore, an attempt was made to find a solution to the interfering effect of the impurities on the quality of caprolactam only on this product, that is by means of catalytic hydrogenation of an aqueous caprolactam solution.

SUMMARY OF THE INVENTION

It has now surprisingly been found that the interfering impurities in the cyclohexanone can be eliminated under mild conditions both in the gas phase and also in the liquid phase under the conditions according to the invention, if a dehydrogenation mixture as described above is used as substrate.

The invention accordingly relates to a process for the purification of cyclohexanone which has been obtained by dehydrogenation of a cyclohexanone/cyclohexanol mixture, which is characterised in that the dehydrogenation mixture is treated in the gas or liquid phase with hydrogen on a hydrogenation catalyst at 20° to 180° C., preferably 50° to 150° C., and at an $H_2$ pressure of 0.1 to 15 bar, preferably 1.1 to 5 bar.

DETAILED DESCRIPTION OF THE INVENTION

The hydrogen can be taken from any desired source. However, preferably, the hydrogen obtained in the preceding dehydrogenation step is used.

The process according to the invention is preferably carried out in the liquid phase. The dehydrogenation mixture is not degassed in this case, but the hydrogen originating from the dehydrogenation and still contained in the liquid dehydrogenation mixture is used. If this hydrogen already present is not sufficient, which can be detected by an insufficient removal of the interfering by-products, further hydrogen is added from an external source. Such external hydrogen can be passed in co-current or counter-current flow to the dehydrogenation mixture to be treated according to the invention.

The hydrogenation catalysts used are those which contain an element of subgroup VIII of the Periodic Table of the Elements (Mendeleev), that is Fe, Co, Ni, Ru, Rh, Pd, Os, Ir or Pt. The noble metals of the platinum group are preferably used, particularly preferably palladium. Such catalysts are disposed on supports, such as $SiO_2$, $Al_2O_3$, pumice and others, in a manner familiar to those skilled in the art. The noble metal content is 0.01 to 10%, preferably 0.1 to 3%, of the total weight of the catalyst. It is further known to those skilled in the art that such hydrogenation catalysts can in addition contain doping and promoter elements, for example Pb, V and others.

Catalysts of this type are used, for example, in the preparation of aniline by gas-phase hydrogenation of nitrobenzene, the aromatic nucleus not being attacked, but the $NO_2$ functional group being reduced to the $NH_2$ group. It is therefore astonishing that, in the cyclohexanone to be purified according to the invention, the keto functional group is conserved.

To carry out the process according to the invention, a simple tubular reactor can be used in which the catalyst is arranged in solid form or as a loose bed. The dehydrogenation mixture to be treated is either pumped from below through the catalyst packing or passed from above over this packing.

The process according to the invention is carried out at 20° to 180° C., preferably at 50° to 150° C. and at a pressure of 0.1 to 15 bar, preferably 1.1 to 5 bar. A residence time of the dehydrogenation mixture on the catalyst, from 2 to 100 minutes, preferably 3 to 30 minutes, is established. The hydrogen added to the dehydrogenation mixture is 0 to 100 parts by volume of $H_2$ under standard conditions per volume of liquid throughput, where, even when the reaction is carried out in the gas phase, this is taken to mean the liquid volume of the dehydrogenation mixture present after the dehydrogenation still in the gaseous state or first in the liquid state and then to be evaporated again. The lower limit of 0 parts by volume of hydrogen indicates that, as already described above, the hydrogen dissolved in the liquid dehydrogenation mixture can be sufficient. Preferably, 0.5 to 5 parts by volume of hydrogen under standard conditions, are added per part by volume of liquid throughput.

A preferred manner of operation is the counter-current procedure, in which hydrogen is passed from below through the catalyst bed and the dehydrogenation mixture to be purified trickles in the liquid phase from above over the catalyst.

It is astonishing and was not predictable that, in a hydrogenation under the abovementioned conditions, no loss of cyclohexanone and no back-hydrogenation to give cyclohexanol occurs. The conversion of unsaturated compounds in the process according to the invention can be up to 99% of their original amount.

EXAMPLES

All experiments were carried out in a metal tube of length 2.85 m and diameter 25 mm. The particular catalyst was introduced between screen plates as a loose bed. The base part of the column was constructed in such a manner that, on the one hand, hydrogen could be introduced there and simultaneously a dehydrogenated crude mixture could be pumped in using the co-current procedure (overflow at the upper column part), or else using the counter-current procedure, so that a post-hydrogenated crude mixture could be discharged via a level controller. In gas phase operation, the hydrogen/-cyclohexanone/cyclohexanol mixture could be introduced into the column both from below and also from above. At the head part of the column there was an inlet or overflow equipped with a cooler/condenser. The corresponding gas and liquid flow rates were measured via rotameters. The conversion was determined from the gas-chromatographically measured concentration changes in each of the substances.

| Example 1 | |
|---|---|
| Anolon, gaseous Rate: | 3.8 l/h |
| Content of unsaturated compounds: | 1201 ppm |
| Hydrogen | |
| Rate: | 2.7 l/h |
| Type: | from dehydrogenation |
| Catalyst: | 2.2% Pd |
| Residence time: | 13 minutes |
| Conversion of unsaturated compounds: | 48% |
| Temperature: | 124° |
| Pressure: | 1.5 bar |
| Example 2 | |
| Anolon, liquid Rate: | 1 l/h |
| Content of unsaturated compounds: | 1331 ppm |
| Hydrogen | |
| Rate: | 5 l/h |
| Type: | Pure |
| Catalyst: | 2.2% Pd |
| Residence time: | 8 minutes |
| Conversion of unsaturated compounds: | 45% |
| Temperature: | 25° |
| Pressure: | 1.1 bar |
| Example 3 | |
| Anolon, liquid Rate: | 7 l/h |
| Content of unsaturated compounds: | 1080 ppm |
| Hydrogen | |
| Rate: | 6 l/h |
| Type: | Pure |
| Catalyst: | 2.2% Pd |
| Residence time: | 14 minutes |
| Conversion of unsaturated compounds: | 92% |
| Temperature: | 68° |
| Pressure: | 1.1 bar |
| Example 4 | |
| Anolon, liquid Rate: | 10 l/h |
| Content of unsaturated compounds: | 1135 ppm |
| Hydrogen | |
| Rate: | 10 l/h |
| Type: | From dehydrogenation |
| Catalyst: | 1.2% Pd + V + Pb |
| Residence time: | 10 minutes |
| Conversion of unsaturated compounds: | 73% |
| Temperature: | 105° |
| Pressure: | 1.3 bar |
| Example 5 | |
| Anolon, liquid Rate: | 10 l/h |
| Content of unsaturated compounds: | 1132 ppm |
| Hydrogen | |
| Rate: | 10 l/h |
| Type: | Pure |
| Catalyst: | 1.2% Pd + V + Pb |
| Residence time: | 10 minutes |
| Conversion of unsaturated compounds: | 83% |
| Temperature: | 105° |
| Pressure: | 1.3 bar |
| Example 6 | |
| Anolon, liquid Rate: | 6 l/h |
| Content of unsaturated compounds: | 883 ppm |
| Hydrogen Rate: | 0 l/h |
| Catalyst: | 2.2% Pd |
| Residence time: | 17 minutes |
| Conversion of unsaturated compounds: | 22% |
| Temperature: | 95° |
| Pressure: | 1.1 bar |
| Example 7 | |
| Anolon, liquid Rate: | 15 l/h |
| Content of unsaturated compunds: | 962 ppm |
| Hydrogen | |
| Rate: | 20 l/h |
| Type: | From dehydrogenation |
| Catalyst: | 0.65% Pd |
| Residence time: | 7 minutes |
| Conversion of unaturated compounds: | 99% |
| Temperature: | 110° |
| Pressure: | 1.3 bar |
| Example 8 | |
| Anolon, liquid Rate: | 15 l/h |
| Content of unsaturated compounds: | 1020 ppm |
| Hydrogen | |
| Rate: | 20 l/h |
| Type: | From dehydrogenation |
| Catalyst: | 0.3% Pd |

-continued

| Residence time: | 7 minutes |
|---|---|
| Conversion of unsaturated compounds: | 97% |
| Temperature: | 110° |
| Pressure: | 1.3 bar |

What is claimed is:

1. A process for the purification of cyclohexanone which has been obtained by dehydrogenation of a cyclohexanone/cyclohexanol mixture, wherein the dehydrogenation mixture is treated in the gas or liquid phase with $H_2$ on a hydrogenation catalyst at 20° to 180° C. and at an $H_2$ pressure of 0.1 to 15 bar.

2. The process of claim 1, wherein the dehydrogenation is carried out at 50° to 150° C.

3. The process of claim 1, wherein the dehydrogenation is carried out at 1.1 to 5 bar.

4. The process of claim 1, wherein the procedure is carried out in the liquid phase.

5. The process of claim 1, wherein the hydrogenation catalyst used is a noble metal/support catalyst having a nobel metal selected from the platinum group.

6. The process of claim 5, wherein the content of noble metal is 0.01 to 10% by weight, relative to the total weight of the catalyst.

7. The process of claim 6, wherein the content of noble metal is 0.1 to 3% by weight, relative to the total weight of the catalyst.

8. The process of claim 1, wherein the treatment is carried out over a time of 2 to 100 minutes.

9. The process of claim 8, wherein the treatment is carried out over a time of 3 to 30 minutes.

10. The process of claim 4, wherein, when the procedure is carried out in the liquid phase, the hydrogen is conducted from below through the catalyst and the liquid dehydrogenation mixture is passed over the catalyst from above.

11. The process of claim 5, wherein the noble metal is palladium.

* * * * *